US006287592B1

(12) United States Patent
Dickinson

(10) Patent No.: US 6,287,592 B1
(45) Date of Patent: Sep. 11, 2001

(54) AQUEOUS DRINK COMPOSITION COMPRISING IBUPROFEN

(75) Inventor: Jeffrey Dickinson, Nottingham (GB)

(73) Assignee: The Boots Company PLC, Nottingham (GB)

( * ) Notice: Subject to any disclaimer, the term of this patent is extended or adjusted under 35 U.S.C. 154(b) by 0 days.

(21) Appl. No.: 09/319,242

(22) PCT Filed: Dec. 9, 1997

(86) PCT No.: PCT/EP97/07137

§ 371 Date: Jun. 7, 1999

§ 102(e) Date: Jun. 7, 1999

(87) PCT Pub. No.: WO98/25595

PCT Pub. Date: Jun. 18, 1998

(30) Foreign Application Priority Data

Dec. 10, 1996 (GB) .................................................. 9625589

(51) Int. Cl.$^7$ ............................ A61K 9/127; A61K 9/14; A61K 9/101; A23C 2/00; A23L 1/05
(52) U.S. Cl. ........................... 424/450; 424/400; 424/489; 424/490; 424/502; 426/590
(58) Field of Search ................................... 424/406, 450, 424/489, 490, 502; 426/590

(56) References Cited

U.S. PATENT DOCUMENTS

| 4,309,421 | * | 1/1982 | Miklos et al. | |
| 4,687,762 | | 8/1987 | Fukusima . | |
| 4,816,247 | | 3/1989 | Desai . | |
| 4,879,108 | * | 11/1989 | Yang et al. | 424/440 |
| 4,882,164 | | 11/1989 | Ferro . | |
| 4,975,465 | | 12/1990 | Motola . | |
| 5,110,606 | * | 5/1992 | Geyer et al. | 426/489 |
| 5,149,655 | * | 9/1992 | Ibsen | 424/489 |
| 5,288,500 | * | 2/1994 | Ibsen | 426/489 |
| 5,407,921 | | 4/1995 | Katsuragi . | |
| 5,653,993 | | 8/1997 | Ghanta . | |
| 5,663,198 | | 9/1997 | Reul . | |
| 5,672,358 | * | 9/1997 | Tabibi et al. | 424/400 |
| 5,681,606 | * | 10/1997 | Hutchinson et al. | 426/590 |
| 5,693,337 | * | 12/1997 | Suzuki et al. | 424/450 |
| 5,741,515 | | 4/1998 | Ciceri . | |
| 5,780,046 | * | 7/1998 | Humber et al. | 424/440 |
| 5,785,976 | * | 7/1998 | Westesen et al. | 424/400 |
| 5,858,410 | * | 1/1999 | Muller et al. | 424/489 |
| 5,871,798 | * | 2/1999 | Hutchinson et al. | 424/590 |
| 5,891,465 | | 4/1999 | Keller . | |

FOREIGN PATENT DOCUMENTS

| 0264187 | | 4/1988 | (EP) . |
| 0274870 | | 7/1988 | (EP) . |
| 0 350 701 | * | 1/1990 | (EP) . |
| 0622072 | | 11/1994 | (EP) . |
| 0700678 | | 3/1996 | (EP) . |
| 8606781 | | 10/1986 | (ES) . |
| 52111533 | | 9/1977 | (JP) . |
| 58059912 | | 4/1983 | (JP) . |
| 59013720 | | 1/1984 | (JP) . |
| 61200909 | | 9/1986 | (JP) . |
| 03176425 | | 7/1991 | (JP) . |
| 9114454 | | 10/1991 | (WO) . |
| 93 20850 | * | 10/1993 | (WO) . |
| 9405260 | | 3/1994 | (WO) . |
| 94 20072 | * | 9/1994 | (WO) . |
| 95 35096 | * | 12/1995 | (WO) . |
| 9718798 | | 5/1997 | (WO) . |

* cited by examiner

Primary Examiner—Shep K. Rose
(74) Attorney, Agent, or Firm—Arent Fox Kinter Plotkin & Kahn, PLLC

(57) ABSTRACT

An ibuprofen composition yielding an aqueous preparation having a pH of less than 7 on the addition of water to said composition which comprises one or more medicaments including an ibuprofen medicament which forms an ibuprofen active ingredient having a melting point less than 100° C., when combined with water to give an aqueous preparation having a pH of less than 7 and a phospholipid material intimately mixed with the ibuprofen medicament. The phospholipid material is capable of forming an aqueous preparation comprising an emulsion or dispersion comprising an aqueous phase substantially free of said ibuprofen active ingredient and a discrete phase consisting essentially of said phospholipid material and insoluble pharmacologically active ingredient including said ibuprofen active ingredient on the addition of water to said composition. The invention also provides aqueous drink preparations (especially heated emulsions) produced therefrom and a process to prepare said aqueous drink preparations.

33 Claims, No Drawings

AQUEOUS DRINK COMPOSITION COMPRISING IBUPROFEN

This application is a 371 application of PCT/EP97/07137 filed Dec. 9, 1997.

This invention relates to compositions useful to produce an aqueous drink preparation containing ibuprofen, to said aqueous drink preparations produced therefrom and to a process to prepare said aqueous drink preparations.

Ibuprofen, namely 2-(4-isobutylphenyl)propionic acid is a well known medicament with analgesic, anti-inflammatory and anti-pyretic properties. It is usually sold in the form of racemic ibuprofen (equal amounts of the S(+)-ibuprofen and R(−)-ibuprofen enantiomers). It may also be in the form of the purified form of either enantiomer, especially S(+)-ibuprofen which is acknowledged to be the active form of racemic ibuprofen. Ibuprofen is also available in salt form, for example the sodium or lysine salt of ibuprofen. Ibuprofen is available under prescription (eg Brufen (RTM)), primarily for the treatment of painful and anti-inflammatory disorders including rheumatoid arthritis, ankylosing spondylitis, osteoarthritis, postoperative pain, post-partum pain and soft tissue injuries, generally at doses of up to 3200 mg per day. Ibuprofen is also available as a non-prescription drug (eg Nurofen (RTM)), primarily for the treatment of symptoms of pain and fever including headache, migraine, rheumatic pain, muscular pain, backache, neuralgia, dysmenorrhoea, dental pain and colds and flu, generally at doses up to 1200 mg per day. Compositions containing ibuprofen are usually provided in unit doses to give 200 mg, 400 mg, 600 mg or 800 mg ibuprofen.

It is desired to formulate a composition containing ibuprofen which on the addition of either cold or hot water (preferably hot water) forms an acceptable liquid product for ingestion by the patient. Such products have particular utility in the treatment of pain and the treatment of coughs and colds but may be desired in any therapeutic area where it is convenient to administer the ibuprofen as a drink. The problem is to provide an easily formulated low cost ibuprofen composition which forms a satisfactory drink product solely by the addition of hot or cold water, ie without requiring extra steps to be taken by the patient before or after adding the water to the ibuprofen composition.

Previously it has not been easy to provide compositions containing ibuprofen which, on the addition of hot water, yield satisfactory aqueous drink preparations ready for substantially immediate administration to the patient. One of the problems associated with ibuprofen is that when dissolved, ibuprofen has an unpleasant taste and an undesirable afterburn sensation in the mouth and throat. Although ibuprofen dissolves more readily in water at a pH above 7, an aqueous drink preparation containing ibuprofen with a pH above 7 does not provide an acceptably tasting product unless additional excipients are added to mask the taste. In order to avoid the cost of, and formulation problems associated with the incorporation of taste-masking ingredients in the composition to allow an acceptably tasting drink product, it is therefore desired to keep the ibuprofen undissolved. Accordingly, the ibuprofen composition should be formulated to ensure that on the addition of water thereto the ibuprofen is maintained as a discrete phase separate from the aqueous phase in the aqueous drink preparation.

In addition, it is desired to be able to formulate a product containing ibuprofen which is adapted, on the addition of water at any temperature, to form a satisfactory aqueous drink preparation which is ready for substantially immediate administration to the patient. This includes both addition of cold water and water at a temperature up to and including its boiling point. The formulation of a product containing ibuprofen which is adapted to form an aqueous drink preparation on combination with cold water is advantageous as cold water is readily available from the tap. On the other hand, the formulation of a product containing ibuprofen which is adapted to form an aqueous drink preparation on combination with hot water is advantageous for the treatment of ailments such as coughs and colds where it is desired to administer ibuprofen in the form of a hot drink.

It has been a particular problem to formulate a product containing ibuprofen capable of producing an aqueous drink preparation on combination with water at a temperature above the melting point of ibuprofen. The particular problem that arises with racemic ibuprofen, is that it has a melting point in the range 75–77° C. The melting point of S(+)-ibuprofen is even lower, approximately 55° C. Accordingly, when combined with cold water, the ibuprofen is in solid form whereas when combined with hot water, eg above the melting point of the drug (ie 77° C. for racemic ibuprofen) the ibuprofen is in liquid form. Thus, means must be provided to ensure that not only does the ibuprofen form a discrete solid phase with water at a temperature less than its melting point but that it is capable of forming and holding a satisfactory emulsion on the addition of hot water (>77° C.) whilst the ibuprofen is undergoing the melting process. Furthermore, if hot water is used, it is necessary to hold the ibuprofen as a homogeneous discrete phase evenly distributed throughout the drink over the period in which the drink may be administered to the patient, eg up to 30 minutes. During this period it is likely that the ibuprofen will cool and solidify. It is still required to maintain the ibuprofen as a discrete phase. Thus, an ibuprofen composition is required which, merely by adding water (preferably hot water) is capable of forming a satisfactory aqueous drink preparation containing ibuprofen and in which the ibuprofen can be maintained as a discrete phase when in the solid state or in the liquid state. Furthermore, it is also desired to provide an ibuprofen composition which forms an acceptably tasting aqueous drink preparation substantially immediately on the addition of water, thus avoiding any waiting time and minimising the need for extra steps such as stirring.

Ibuprofen compositions adapted to form drink products on the addition of hot water have previously been proposed. For example WO 93/20850 discloses compositions to which hot water may be added. However, this disclosure requires significant formulation steps to prepare a soluble ibuprofen-beta-cyclodextrin complex which dissolves on the addition of water.

The formation of a dispersion of ibuprofen with cold water has previously been proposed (see European Patent Application Nos. 284167 and 390369). However, the compositions disclosed therein are not adapted to provide satisfactory aqueous preparations on the addition of hot water due to the formation of an oily slick of melted ibuprofen at the surface of the water.

Other proposals have also been made to keep the ibuprofen as a discrete phase in an aqueous preparation. For example, microcapsules, in which NSAID are encapsulated within a polymer wall, are disclosed in WO 95/05166. Although these can be formulated as liquid aqueous suspensions, it does not indicate that it would be suitable to add hot water to these microcapsules. Also such microcapsules require complex preparation steps which the composition of the present invention seeks to avoid. Other means of maintaining ibuprofen as a discrete phase are disclosed in European Patent Application 274870 which discloses that NSAID drugs such as ibuprofen may be formulated with surfactants such as polyethoxylated nonionics or sorbitan fatty acid esters to give micelle-forming compositions. The surfactant is required in considerable excess (ie greater than five times the amount of active ingredient). This is unsatisfactory for a relatively high dose drug such as ibuprofen (eg 100–400 mg doses) due to the large amount of surfactant required.

The formation of liposomes using phospholipid materials has been proposed in which a drug is encapsulated in a liposome (a lipid bilayer membrane) in an aqueous formulation. See for example European Patent Application 622072 which discloses the formation of liposomes based on yolk lecithin and soybean lecithin as lipids, which dispersion also contains at least one hydroxy acid and at least one amino acid to stabilise the liposome dispersion. However, the encapsulation of a drug in the bilayer membrane also requires complex preparative steps which the compositions of the present invention seek to avoid.

The formation of lipid emulsions containing phospholipids in which the active ingredient is mixed with a lipid material in the oily phase have also been proposed. For example, European Patent Application No. 700678 discloses a stable lipid emulsion comprising (a) an oil component such as vegetable oils and/or synthetic or semisynthetic glycerides, (b) an emulsifying agent containing yolk lecithin and/or soybean lecithin, (c) water, (d) drug, (e) citric acid and (f) selected amino acids. U.S. Pat. No. 5,110,606 also discloses an emulsion comprising as the internal phase a drug contained in particular polar liquid carriers, the internal phase being dispersed in a lower alkyl ester of a $C_8$–$C_{12}$ fatty acid external phase using lecithin as an emulsifying agent, wherein the ratio of components is 1–20% polar liquid, 33–70% fatty ester and 20–60% lecithin. These methods disclose relatively complex stages and/or a significant number of formulation excipients to formulate these aqueous preparations.

There is no disclosure of how to formulate a simple ibuprofen composition which can be used to provide a stable aqueous preparation on the addition of hot water and maintain ibuprofen as a discrete phase taking into account its melting point characteristics.

The formation of an emulsion with melted ibuprofen and a surfactant has been proposed. However, Japanese Patent Application 52111533 discloses that is necessary to first add the ibuprofen to a solution of a polyoxyethylene derivative surfactant in hot water followed by heating the mixture to melt the ibuprofen and then cooling to cause precipitation out of the ibuprofen. The ibuprofen is then collected and dried and then taken for further formulation. This disclosure does not suggest that a satisfactory unit dose aqueous formulation could be produced for substantially immediate administration to a patient merely by adding hot water to a composition comprising the active ingredient.

It has also been proposed in WO 9420072 that low melting point drugs such as ibuprofen may be melted with lipid material such as lecithin and hot water added, but this also involves a complex process in which the solid lipid is melted, stabilisers are added either to the lipid and the dispersion medium or to the dispersion medium only; the drug is then incorporated into the lipid particles (optionally by melting) and the dispersion medium is heated to the temperature of the melt; finally the melted lipid compound containing the drug is emulsified in the dispersion medium, preferably by high speed homogenisation. This disclosure also does not suggest the provision of an emulsion-forming composition which yields an aqueous drink formulation substantially immediately on the addition of hot water.

These disclosures suggest that when the melting characteristics of ibuprofen are taken into account, complex formulation steps are necessary to form an emulsion of this drug. They provide no suggestion as to how to provide a simple relatively low cost composition to which hot water can be added to provide an acceptably tasting product without the occurrence of ibuprofen's characteristic oily slick on the surface of the water.

We have now found an ibuprofen composition capable of forming a discrete phase containing only ibuprofen and a certain phospholipid material which can be formulated easily giving an acceptably-tasting, stable aqueous preparation substantially immediately on the addition of hot or cold water to the ibuprofen composition. The composition comprises an intimate combination of an ibuprofen medicament and a phospholipid material and is adapted to form an acidic preparation on combination with water at a temperature in the range 0–100° C.

In this specification, certain expressions have the meanings set out below. "medicament" means any pharmacologically active substance providing a therapeutic effect. The medicaments may be formed into a different ionic species when in an aqueous medium at acidic pH, thus we refer herein to the "pharmacologically active ingredient" as being the form of the medicament when dissolved, dispersed or emulsified in water at a pH of less than 7.

"ibuprofen composition" means a pharmaceutical composition containing the ibuprofen medicament which on combination with water at a temperature in the range 0–100° C. produces an aqueous preparation having a pH of less than 7.

"ibuprofen active ingredient" means the form of ibuprofen having a melting point below 100° C. which is present in the discrete phase of an acidic aqueous preparation after the ibuprofen composition has been combined with water at a temperature in the range 0–100° C.

"ibuprofen medicament" means the form of the ibuprofen which is present in the ibuprofen composition and which forms the ibuprofen active ingredient when an aqueous preparation having a pH of less than 7 is formed by combining the ibuprofen composition with water at a temperature in the range 0–100° C. The ibuprofen medicament may therefore be ibuprofen itself or a derivative of ibuprofen which forms the ibuprofen active ingredient on combination with water at a temperature in the range 0–100° C. to give an aqueous preparation having a pH of less than 7. Such derivatives include, but are not limited to, salts, optical isomers and hydrates. The salt derivatives form ibuprofen as the ibuprofen active ingredient in-situ on the addition of water at a pH less than 7. Suitable salts of ibuprofen include the alkali metal salts such as the sodium and potassium salts; the amino acid salts such as the lysine or arginine salts, or amine salts such as the meglumine salt. The ibuprofen may either be in racemic form or in the form of the S(+)- and R(−)-enantiomers or of mixtures of these enantiomers. The preferred enantiomer is S(+)-ibuprofen which is acknowledged to be the therapeutically effective enantiomer. The present invention also applies to both anhydrous and hydrated forms of the ibuprofen medicament, for example the monohydrate and dihydrate of a salt (eg the sodium salt) of ibuprofen. Preferably, the ibuprofen medicament comprises racemic ibuprofen or substantially pure S(+)-ibuprofen, more preferably racemic ibuprofen.

"aqueous preparation" means the preparation intended to be ingested by the patient produced when the ibuprofen composition is combined with water at a temperature in the range 0–100° C. The aqueous preparation comprises an aqueous phase substantially free of ibuprofen active ingredient and a discrete phase incorporating substantially all of the ibuprofen active ingredient. The aqueous phase may contain soluble pharmacologically active ingredients dissolved therein. The aqueous preparation may be in the form of a dispersion of the ibuprofen active ingredient. By the term "dispersion", we mean that the ibuprofen active ingredient is suspended in solid form as the dispersed phase uniformly distributed throughout the aqueous phase. When another higher melting point insoluble pharmacologically active ingredient is used, when hot water is added there may be formed a dispersion wherein liquid ibuprofen active ingredient is mixed with solid pharmacologically active ingredient. The dispersed phase consists essentially of insoluble pharmacologically active ingredient, including the ibuprofen active ingredient, and the phospholipid material. The aqueous preparation may also be in the form of an emulsion of the ibuprofen active ingredient. By the term "emulsion", we mean an oil-in-water emulsion in which the ibuprofen active ingredient, optionally with another liquid pharmacoligically active ingredient, is suspended in liquid form as the oily phase uniformly distributed throughout the aqueous phase. The oily phase consists essentially of insoluble pharmacologically active ingredient, including the ibuprofen active ingredient and the phospholipid material. "discrete" means that the phase containing the insoluble pharmacologically active ingredient including the ibuprofen active ingredient, is separate and distinct from the aqueous phase. The ibuprofen active ingredient is not dissolved in the aqueous phase. However, it is dispersed uniformly throughout the aqueous phase. It is maintained as a separate and distinct phase from the aqueous phase by the phospholipid material. As defined herein, the discrete phase consists essentially of insoluble pharmacologically active ingredient, including ibuprofen active ingredient and phospholipid material.

"insoluble" means insoluble in water at a pH of less than 7.

The present invention provides an ibuprofen composition comprising one or more medicaments including an ibuprofen medicament which forms an ibuprofen active ingredient having a melting point less than 100° C. when combined with water to give an aqueous preparation having a pH of less than 7, characterised in that the composition yields an aqueous preparation having a pH of less than 7 on the addition of water to said composition and comprises a phospholipid material intimately mixed with the ibuprofen medicament, said phospholipid material being capable of forming an aqueous preparation (eg comprising an emulsion or dispersion) comprising an aqueous phase substantially free of said ibuprofen active ingredient and a discrete phase consisting essentially of said phospholipid material and insoluble pharmacologically active ingredient including said ibuprofen active ingredient on the addition of water to said composition.

In a further aspect the present invention provides a unit dose aqueous preparation comprising an aqueous phase and a discrete phase comprising (a) an ibuprofen active ingredient having a melting point of less than 100° C. and (b) a phospholipid material capable of forming said ibuprofen active ingredient into a discrete phase on combination with water, characterised in that the aqueous preparation has a pH of less than 7 and that said aqueous phase is essentially free of said ibuprofen active ingredient and that said discrete phase consists essentially of said phospholipid material and insoluble pharmacologically active ingredient including said ibuprofen active ingredient.

Particular advantages achieved by the present invention are the provision of a composition that can be easily formulated by the manufacturer and an acceptably tasting drink product that can be prepared very easily by the patient together with the use of minimal quantities of homogenising excipients. It is especially advantageous that a hot drink can be prepared merely by adding hot water to the ibuprofen composition. The present invention also provides a liquid formulation from which absorption of ibuprofen into the body is optimised, ie the ibuprofen phase is uniformly distributed throughout the aqueous preparation.

Racemic ibuprofen and S(+)-ibuprofen are the preferred ibuprofen active ingredients. When the ibuprofen active ingredient is racemic ibuprofen the water added should preferably be at a temperature in the range 80–100° C., preferably 90–100° C. When the ibuprofen active ingredient is S(+)-ibuprofen, the water added should preferably be at a temperature in the range 60–100° C., preferably 80–100° C. Preferably when the aqueous phase is at a temperature above the melting point of the ibuprofen active ingredient, the discrete oily phase consists essentially of said phospholipid material and liquid ibuprofen active ingredient. More preferably the discrete oily phase consists essentially of said phospholipid material and ibuprofen either as racemic ibuprofen or S(+)-ibuprofen.

The aqueous preparation formed on the addition of water to the ibuprofen composition comprises an aqueous phase and also a discrete phase incorporating the ibuprofen active ingredient. The aqueous phase comprises a sufficient quantity of water to form a drink. The quantity of water to be added to the ibuprofen composition is therefore such as to provide an acceptable aqueous drink preparation. The lower amount of the quantity of water is usually determined by the dosage of ibuprofen, for example a low dosage such as 100 mg requires less water to form a uniform dispersion or emulsion than a dose of 400 mg ibuprofen. The upper end of the range is determined by the quantity of water that a person is prepared to drink for a single unit dose. Generally, it is anticipated that the amount of water will be in the range 10 ml–500 ml, more preferably 50–300 ml, most preferably 100–250 ml.

The phospholipid material provides the interface between the water and the ibuprofen active ingredient such that the discrete phase is stable and retains its homogeneous microfine structure in the aqueous phase. The phospholipid material and optional surfactants provide the interface between the discrete phase and the external aqueous phase. The phospholipid material suspends the ibuprofen active ingredient as a discrete phase in the aqueous phase.

Other suspended or dispersed components may also be present in the aqueous preparation in addition to the discrete phase consisting essentially of the insoluble pharmacologically active ingredient. Preferably, the ibuprofen composition contains only water-soluble excipients other than the medicament or medicaments, so that all the excipients dissolve in the water when it is combined with the ibuprofen composition. However, it may contain insoluble materials such as certain cellulose materials which are dispersed in the aqueous phase and do not form part of the discrete phase consisting essentially of said phospholipid material and insoluble pharmacologically active ingredient including ibuprofen active ingredient. Such other ingredients may aid in stabilising the emulsion and/or modifying the viscosity of the emulsion. Preferably, the ibuprofen medicament is the only substantially insoluble medicament employed and more preferably is the only substantially insoluble component in the ibuprofen composition.

The amount of the ibuprofen medicament in the ibuprofen composition will depend on the required treatment regimen. Administration of the aqueous preparation obtained from the ibuprofen composition may only be once daily or it may be several times daily, for example 2–4 times daily, for as long as the treatment is required. Each dosage unit of the ibuprofen composition suitably contains the ibuprofen medicament in an amount to give an equivalent dosage of 50–800 mg ibuprofen, preferably 100–400 mg and most preferably 100–200 mg ibuprofen per unit dose. When S(+)-ibuprofen is used alone, these quantities may be reduced, eg suitably 25–800 mg, preferably 50–300 mg and more preferably 100–200 mg S(+)-ibuprofen. If required two or more dosage units (eg tablets, sachets of granules, spoonfuls) of the ibuprofen composition may be taken and the water added thereto. Thus, the ibuprofen composition may contain the ibuprofen medicament in smaller quantities than the amounts given above such that more than one dosage unit of the ibuprofen compositions may be used.

If desired, a further medicament may be employed. The pharmacologically active ingredient, produced from said further medicament on the addition of water to provide an acidic aqueous preparation, could be dissolved or dispersed in either the discrete phase or the aqueous phase. The soluble pharmacologically active ingredient or ingredients will form part of the aqueous phase. The insoluble pharmacologically active ingredient or ingredients will form the discrete phase. Examples of further medicaments include any ingredient commonly used in a cough or cold remedy, for example, an antihistamine, caffeine or another xanthine derivative, a cough suppressant, a decongestant, an expectorant, a muscle relaxant, a vitamin and a co-analgesic such as codeine or another NSAID or combinations thereof. Suitable antihistamines which are preferably non-sedating include acrivastine, astemizole, azatadine, azelastine, bromodiphenhydramine, brompheniramine, carbinoxamine, cetirizine, chlorpheniramine, cyproheptadine, dexbrompheniramine dexchlorpheniramine, diphenhydramine, ebastine, ketotifen, lodoxamide, loratidine, levocubasstine, mequitazine, oxatomide, phenindamine, phenyltoloxamine, pyrilamine, setastine, tazifylline, temelastine, terfenadine tripelennamine or triprolidine. Suitable cough suppressants include caramiphen, codeine (codeine phosphate) or dextromethorphan. Suitable decongestants include pseudoephedrine, phenylpropanolamine and phenylephrine. Suitable expectorants include guaiphenesin, potassium citrate, potassium guaiacolsulphonate, potassium sulphate and terpin hydrate. Suitable vitamins include vitamin C. Preferably a water-soluble medicament is employed so that the further medicament is present in the aqueous phase of the liquid preparation. The amounts of these other pharmacologically active ingredients to be used are those known to those skilled in the art. For guidelines as to suitable dosage, reference may be made to MIMS, the Physicians Desk Register and the OTC Handbook.

The ratio of aqueous phase to discrete phase will depend on the dosage of the ibuprofen medicament used, but suitably the ratio of aqueous phase to discrete phase will fall within the range 10,000:1 to 1:1 parts by weight, more preferably 5000:1 to 100:1 and most preferably 2000:1 to 500:1 parts by weight. The water may be added in a ratio to the ibuprofen composition of 10,000:1 to 1:1 parts by weight, preferably 5000:1 to 100:1 parts by weight, more preferably 2000:1 to 500:1 parts by weight.

Depending on the nature of the ibuprofen medicament, the dosage required and the form of the ibuprofen composition, the ibuprofen medicament may form 1–99% by weight, desirably 2–80% by weight of the ibuprofen composition. The ibuprofen composition may be in solid form (eg tablets, powders, granules etc) or liquid form. When the ibuprofen composition is in the form of a tablet, preferably the ibuprofen medicament is present to an extent of 50–80% by weight, especially 55–70% by weight, of the composition. When the ibuprofen composition is in powder form, eg as a fine powder or as granules, preferably the ibuprofen medicament is present to an extent of 3–20% by weight, especially 4–10% by weight, of the composition. When the ibuprofen composition is in the form of a liquid concentrate, preferably the ibuprofen medicament comprises 1–10% by weight, more preferably 2–5% by weight, of the composition.

The phospholipid material selected is capable of forming the ibuprofen active ingredient into a discrete phase on combination with water to give an aqueous preparation having a pH of less than 7 at any temperature between 0 and 100° C. When the water is at a temperature at or below the melting point of the lowest melting point insoluble drug (usually the ibuprofen active ingredient), a dispersion will be formed in which the dispersed phase consists essentially of said phospholipid material and insoluble pharmacologically active ingredient including the ibuprofen active ingredient. When the water is at a temperature above the melting point of the highest melting point insoluble drug (usually the ibuprofen active ingredient), an emulsion will be formed in which the oily phase consists essentially of said phospholipid material and insoluble pharmacologically active ingredient including the ibuprofen active ingredient. The phospholipid material includes both naturally occurring and synthetic phospholipids. We prefer to use lecithin materials or phosphatide materials. Examples include soya bean lecithin, egg lecithin, vegetable lecithin and hydrogenates thereof, dimyristoylphosphatidylcholine, dipalmitoylphosphatidylcholine, distearoylphosphatidylcholine, diacetylphosphate, phosphatidylglycerol, phosphatidylethanolamine, phosphatidylserine, phosphatidylinositol, phosphatidylcholine and sphingomyelin. Lecithin is a complex mixture of phosphatides, which consist chiefly of phosphatidylcholine, phosphatidylethanolamine, phosphatidylserine and phosphatidylinositol, combined with various amounts of other substances such as triglycerides, fatty acids and carbohydrates as separated from a crude vegetable source. The composition of lecithin varies according to the source and the degree of purification. Egg lecithin contains 69% phosphatidylcholine and 24% phosphatidylethanolamine, whilst soybean lecithin contains these ingredients in amounts of 21% and 22% respectively, together with 19% phosphatidylinositol. Lecithins are practically insoluble in water but on mixing with water they hydrate to form emulsions. Particular advantages are obtained by using the natural lecithin materials identified above (see also the Excipients Handbook, 2nd Edition 1994, Ed A Wade and P J Weller). Preferably a single phospholipid material is employed, most preferably a naturally occurring lecithin. In a particularly preferred aspect we use soybean lecithin.

A further advantage lies in the fact that only a small proportion of the phospholipid material is necessary to achieve the aqueous preparations of the present invention. Preferably the phospholipid material is used to an extent of less than 10% by weight of the ibuprofen active ingredient in accordance with the present invention. This is advantageous as it is desired to formulate dosage forms with minimal excipients.

The quantity of phospholipid will depend on the form of the ibuprofen composition and on the nature and dosage of the ibuprofen medicament. Preferred compositions comprise the phospholipid material in a ratio to ibuprofen medicament of 0.001:1 to 0.5:1 parts by weight, more preferably, 0.01:1 to 0.3:1 parts by weight, most preferably 0.02:1 to 0.2:1 parts by weight, especially 0.03 to 0.07 parts by weight. Preferred compositions contain a phospholipid material in an amount less than 10% by weight, for example 0.01–5%, by weight, more preferably 0.025–2% by weight of the ibuprofen composition especially 0.1–1.5% by weight of the ibuprofen composition.

It is often advantageous to use one or more non-phospholipid surfactants in combination with the phospholipid material to achieve the desired emulsifying effect. Advantageously, surfactants solid at ambient temperature are employed. Examples, include, but are not limited to, one or more ingredients such as sodium lauryl sulphate, sorbitan esters, polyoxyethylene alkyl ethers, poloxamer, polyoxyethylene castor oil derivatives, polyoxyethylene sorbitan fatty acid esters. Preferably sodium lauryl sulphate is used as the surfactant. Conveniently the surfactant is used in an amount less than 10% by weight, for example 0.01–5% by weight, more preferably 0.025–2% by weight, especially 0.1–1.5% by weight of the ibuprofen composition. Preferably, if a surfactant is included in the composition it will be present in a ratio to the phospholipid material of 10:1 to 1:10 parts by weight, preferably 5:1 to 1:5 parts by weight.

The aqueous preparations formed in accordance with the invention are acidic, namely they have a pH of less than 7. We have found that by ensuring that the aqueous preparation is at acidic pH and the ibuprofen active ingredient is kept within the discrete phase, a palatable drink formulation is provided. In some cases the preparation formed will have a pH of 7 or less by the choice of active ingredient(s) and optional excipients used. However, when the ibuprofen salts or other derivatives selected are likely to yield a pH greater than 7, eg the sodium or potassium salts, the ibuprofen composition should contain an acidic component which provides an aqueous preparation having a pH of 7 or less. Ordinarily, when water is added to such an ibuprofen composition, ibuprofen would be caused to precipitate out and form an unsatisfactory dispersion. However, in accordance with this invention, the ibuprofen is formed into the discrete phase by the phospholipid material. Accordingly, in a preferred aspect the incorporation of suitable amounts of an acidic component ensures that the resulting aqueous preparation has an acidic pH. Thus, a further preferred component of the ibuprofen composition is an acidic component. Such a component ensures that the liquid preparation formed on the addition of water has a pH less than 7, preferably less than 6, more preferably less than 5 and most preferably less than 4.5. Examples of the acidic component include one or more of citric acid, tartaric acid or malic acid, or salts thereof such as sodium citrate. Preferably the acidic component is a buffer system used to maintain the pH at less than 7 during administration. Examples of suitable buffer systems include citric acid together with sodium citrate.

When used the acidic component may suitably form up to 35% of the dosage form for example, 1–30% by weight, preferably 5–28% by weight or preferably 10–25% by weight of the ibuprofen composition. It may be used in a ratio to ibuprofen medicament of 1:20 to 20:1 parts by weight, preferably 1:10 to 10:1 parts by weight, most preferably 8:1 to 1:1 parts by weight.

The ibuprofen composition may either be in solid or liquid form and it may contain such other pharmaceutically acceptable excipients as are necessary to make an acceptable composition, dispersion and emulsion.

It is preferred to use a water soluble carrier material to carry the ibuprofen medicament and phospholipid material and to aid the formation of the aqueous preparation. The carrier material is intimately mixed with the ibuprofen medicament and the phospholipid material in the ibuprofen composition such that the materials form a homogeneous blend. Examples of water soluble carriers include sugars including monosaccharides, polysaccharides and sugar alcohols, for example caster sugar, sorbitol, mannitol, xylitol, maltodextrin, lactose, sucrose, fructose, dextrin, glucose and cyclodextrin as well as polyethylene glycols. The amount of water soluble carrier, preferably a sugar component, used will depend on the form of the composition and the necessary dosage. Suitably it may be used to an extent of 1–99% w/w of the ibuprofen composition, preferably 5–80% w/w, more preferably 10–70% w/w and most preferably 20–65% w/w of the ibuprofen composition.

When in the form of a liquid, the ibuprofen medicament may be dissolved or suspended in the solvent to form a syrup or concentrate. Water may be added to the syrup or concentrate to form the liquid drink preparation. Suitable liquid carriers for combination with the active ingredient include alcohols, glycols and edible oils. In addition, the liquid ibuprofen composition may also comprise viscosity modifiers, gelling agents, flavours, sweeteners and colours.

Preferably the ibuprofen composition is in solid form, eg as a powder, granule or tablet. Optional formulation aids may be used, such as a disintegrant, eg croscarmellose sodium, starch and starch derivatives, (preferably in an amount up to 10% by weight, eg 1–10% by weight, more preferably 2–8% by weight, of the composition), a binder, eg polyvinylpyrrolidone, HPMC, starch and its derivatives (preferably in an amount up to 5% by weight, eg 1–5% by weight, more preferably 2–4% by weight, of the composition), tabletting aids such as a compressible binder eg microcrystalline cellulose (preferably in an amount up to 20% by weight, eg 5–20% by weight of the composition), a flow aid such as colloidal silica and silica derivatives, (preferably in an amount up to 3% by weight, eg 0.1–3% by weight, more preferably 0.5–2% by weight, of the composition), a lubricant such as stearic acid or magnesium stearate, (preferably in an amount up to 3% by weight, eg 0.1–3% by weight, more preferably 0.5–2% by weight, of the composition), and flavouring aids, sweeteners, colouring aids etc as required.

The discrete phase which may be the dispersed phase in a dispersion or the oily phase in an emulsion may optionally include a minimal proportion of water-insoluble material, immaterial to the present invention, such as a lipid or other hydrophobic ingredient, suspended in the active ingredient. Examples are well-known to those skilled in the art and include mono-, di and triglycerides of long chain fatty acids, fatty acid esters, waxes, vegetable oils, insoluble cellulose materials and insoluble cross-linked polyvinylpyrolidone. Such materials may suitably form up to 10% by weight of the active ingredient, for example 0–5% by weight of the active ingredient. Preferred compositions contain none or negligible amounts of such materials.

The aqueous preparation is formed by combining the ibuprofen composition with water at any temperature in the range 0–100° C. If ibuprofen is the sole medicament or any other medicament employed has a higher melting point, when the ibuprofen composition is combined with water at a temperature below the melting point of the ibuprofen active ingredient an aqueous preparation in the form of a dispersion is formed. In most cases the water will be at a temperature in the range 5–50° C., more preferably 10–30° C. When at temperatures above ambient temperature (eg greater than approximately 25° C.), the water will require to be heated. On combining the water with the composition, the aqueous preparation is formed substantially immediately and is ready for immediate administration to the patient. When the ibuprofen composition is combined with water heated to a temperature above the melting point of the ibuprofen active ingredient an aqueous preparation wherein the ibuprofen active ingredient is in liquid form is formed. The ibuprofen composition itself does not require a preheating stage before mixing with the heated water. In most cases the ibuprofen active ingredient will have the lowest melting point as most drugs have a melting point above 100° C. The temperature of the water when combined with the ibuprofen composition is in the range defined by the melting point of the ibuprofen active ingredient and the boiling point of water. Preferably the water is at a temperature in the range between at least 5° C. or 10° C. above the melting point of the ibuprofen active ingredient and 100° C. In most cases, the water will be at a temperature in the range 50–100° C., preferably 60–100° C., more preferably 70–100° C. and most preferably 80–100° C. On combining the heated water with ibuprofen composition, the aqueous preparation is formed substantially immediately and is ready for immediate administration to the patient, provided that the temperature of the liquid is not too hot. If necessary the aqueous preparation may be stirred after combination with the heated water to aid the formation of the emulsion. If the water has been heated to its boiling point, the patient may desire to wait a short time (eg 5–10 minutes) whilst the aqueous preparation cools to an acceptable temperature for administration.

Preferably the aqueous preparation is formed by placing a unit dose of the ibuprofen composition (eg in a solid form, for example a tablet or granules, or in liquid form, for example a liquid concentrate) in a receptacle and adding the water. This is a very simple means of administering the active ingredient and forms another particular advantage of the present invention. Alternatively, the unit dose of the ibuprofen composition may be added to a receptacle already containing water. Preferably, the water is added directly to the ibuprofen composition.

In another aspect, the invention provides a process to make a unit dose aqueous preparation comprising an aqueous phase substantially free of ibuprofen and a discrete phase incorporating ibuprofen characterised by the step of combining an ibuprofen composition comprising an intimate mixture of:

(a) one or more medicaments including an ibuprofen medicament which forms an ibuprofen active ingredient having a melting point less than 100° C. when combined with water to give an aqueous preparation having a pH of less than 7, (b) a phospholipid material capable of forming said ibuprofen active ingredient into a discrete phase on combination of the ibuprofen composition with water; and, if required, (c) an acidic component adapted to yield an aqueous preparation having a pH of less than 7, with water, wherein the combination of said water with said ibuprofen composition causes an aqueous preparation having a pH of less than 7 to be formed substantially immediately wherein the discrete phase consists essentially of said phospholipid material and insoluble pharmacologically active ingredient including said ibuprofen active ingredient.

In a preferred process, there is provided an emulsion by combining said ibuprofen composition with water at a temperature above the melting point of the ibuprofen active ingredient.

Further preferably, there is provided a process to emulsify an active ibuprofen ingredient in an aqueous medium which comprises the steps of:

(1) heating a quantity of water to a temperature in the range defined by the melting point of the active ibuprofen ingredient and the boiling point of water;

(2) combining said heated water with an ibuprofen composition comprising an intimate mixture of (a) an ibuprofen medicament which forms an ibuprofen active ingredient having a melting point less than 100° C. when combined with water to give an aqueous preparation having a pH of less than 7, (b) a phospholipid material capable of emulsifying the active ibuprofen ingredient on combination of the ibuprofen composition with water at a temperature in the range defined by the melting point of the active ibuprofen ingredient and the boiling point of water, and optionally if required (c) an acidic component adapted to yield an aqueous preparation in the form of an emulsion having a pH of less than 7, wherein the combination of said ibuprofen composition with said heated water causes the substantially immediate formation of a uniform aqueous emulsion having a pH of less than 7 wherein the oily phase consists essentially of said phospholipid material and ibuprofen active ingredient.

The preferred aqueous preparations in the form of emulsions formed in accordance with the invention are formed as microfine uniform emulsions substantially immediately on the addition of water at a temperature at or above the melting point of the active ibuprofen ingredient. Furthermore, on cooling, as the active ibuprofen ingredient solidifies, the solid particles do not coalesce but are retained in the form of a fine dispersion. This is an advantage as, if boiling water is used to make the aqueous preparation in the form of emulsion, the patient may require the aqueous preparation to cool to a temperature below the melting point of the active ibuprofen ingredient before drinking it. Such dispersions formed from the aqueous emulsions of the present invention have been found to be stable for up to 24 hours.

The aqueous preparations of the present invention comprising emulsions or dispersions are pleasant-tasting and therapeutically effective. As they are presented in an aqueous preparation they are thus available for absorption on ingestion by swallowing the drink product. Ibuprofen and its derivatives are primarily anti-inflammatory, analgesic and anti-pyretic agents, but have also been proposed for other therapeutic uses, eg to treat periodontal bone loss, pruritus, Alzheimer's disease etc. The aqueous preparations of the present invention are therefore indicated for use in the treatment of all therapeutic uses for which ibuprofen is effective, including rheumatoid arthritis, osteoarthritis and ankylosing spondylitis, seronegitive arthropathies, periarticular disorders and soft tissue injuries. They may also be used in the treatment of post-operative pain, post-partum pain, dental pain, dysmenorrhoea, headache, migraine, rheumatic pain, muscular pain, back ache, neuralgia and/or mucsoskeletal pain or the pain or discomfort associated with the following: respiratory infections, colds or influenza, gout or morning stiffness.

Accordingly, in a further aspect the present invention provides a method of obtaining a therapeutic response, preferably an anti-inflammatory, analgesic and/or anti-pyretic response, comprising administering to a person in need thereof a unit dose aqueous preparation comprising an aqueous phase and a discrete phase comprising (a) an ibuprofen active ingredient having a melting point of less than 100° C. and (b) a phospholipid material capable of forming said ibuprofen active ingredient into a discrete phase on combination with water, characterised in that the aqueous preparation has a pH of less than 7 and that said aqueous phase is essentially free of said ibuprofen active ingredient and that said discrete phase consists essentially of said phospholipid material and pharmacologically active ingredient including said ibuprofen active ingredient.

In another aspect the invention provides a process to prepare an ibuprofen composition adapted to provide an aqueous preparation, having an aqueous phase substantially free of ibuprofen and a discrete ibuprofen phase on the addition of water at a temperature in the range 0–100° C., comprising:

(a) forming an intimate mixture of one or more medicaments, including an ibuprofen medicament which forms an ibuprofen active ingredient having a melting point less than 100° C. on combination of said ibuprofen medicament with water to give an aqueous preparation having a pH of less than 7, with a phospholipid material capable of forming an aqueous preparation comprising an emulsion or dispersion wherein the discrete phase consists essentially of said phospholipid material and insoluble pharmacologically active ingredient including an ibuprofen active ingredient, optionally with other excipients; and (b) formulating said mixture into a unit dose composition.

In the formulation of the composition, the combining and blending process may be a single stage with all the solid components introduced into a blender and mixed until a homogeneous blend is achieved. Alternatively, the ibuprofen may be granulated with the phospholipid material together with another surfactant and optionally other ingredients, to form a granule which may then be dried and then combined with the remaining excipients to form a homogeneous mixture. Alternatively the granules may be milled to form a powder which is combined with the remaining excipients to form a homogeneous mixture. The granulation stage or blending may either be carried out dry or with a liquid binder, such as a solvent system containing polyvinylpyrrolidone or with an aqueous binder such as ethanol in water. These may either then be fed directly into appropriate storage means as powders or granules (e.g. into sachets) or fed to a tabletting machine for compression into tablets.

The invention is illustrated by the following non-limitative Examples.

In the Examples, soybean lecithin is supplied by Lucas Meyer, Germany under the trade name Emultop®. The egg lecithin is also supplied by Lucas Meyer, Germany.

EXAMPLE 1

| Ibuprofen | 200 mg |
| Caster sugar | 2500 mg |
| Citric acid | 500 mg |
| Sodium citrate | 400 mg |
| Flavour | 400 mg |
| Sodium lauryl sulphate | 10 mg |

-continued

| Colouring agent | 10 mg |
| Sweetener | 42 mg |
| Soybean tecithin | 10 mg |

The ibuprofen and soybean lecithin were milled together and then blended with the remaining powder excipients until a homogeneous mixture was obtained. The mixture was then packed into sachets to yield 200 mg ibuprofen per sachet.

The contents of the sachet were placed into a cup and 200 ml substantially boiling water added. The ibuprofen melted and was immediately emulsified to form a satisfactory drink formulation. The emulsified phase was present as small droplets distributed evenly throughout the drink to give satisfactory slightly cloudy homogeneous appearance. No oily slick of ibuprofen was formed on the surface. The formulation was allowed to cool slightly and was then ready for administration to the patient as a drink. The emulsion was maintained on cooling (e.g. over 30 minutes).

200 ml cold water was added to a further sachet containing the above composition. A dispersion was immediately formed to yield a satisfactory drink product.

Smaller quantities of hot water (e.g. >85° C.), warm (40–85° C.), or colder (e.g. <40° C.) water, such as 150 ml, 100 ml and 50 ml may be added to the granular mixture to form an emulsion/dispersion.

The granular mixture may also be prepared by granulating the ibuprofen, soybean lecithin and sodium lauryl sulphate in a high speed mixture using aqueous ethanol as the granulating liquid. The resulting granules may then be dried and milled to produce a fine powder. The powder may be added to the remaining excipients and blended until a homogeneous mixture is obtained. The mix may then be packed into sachets to yield 200 mg ibuprofen per sachet.

EXAMPLES 2–5

In the same way as described for Example 1, a granular mixture containing ibuprofen or a derivative thereof was prepared.

| Ingredients | Example 2 | Example 3 | Example 4 | Example 5 |
|---|---|---|---|---|
| Racemic ibuprofen | — | — | 200 mg | 200 mg |
| Racemic Ibuprofen (sodium salt) | 256 mg | — | — | — |
| S(+)-ibuprofen | — | 100 mg | — | — |
| Refined sugar | 2500 mg | 2500 mg | 2500 mg | 2500 mg |
| Citric acid | 500 mg | 500 mg | 500 mg | 500 mg |
| Sodium citrate | 400 mg | 400 mg | 400 mg | 400 mg |
| Sodium lauryl sulphate | 10 mg | 10 mg | 10 mg | 10 mg |
| Sweetener | 35 mg | 35 mg | 35 mg | 35 mg |
| Soybean lecithin | 10 mg | 10 mg | — | — |
| Egg lecithin | — | — | 10 mg | 50 mg |

Results: Examples 2–3

The contents of the sachet were placed into a cup and 200 ml very hot water (>95° C.) added. The ibuprofen melted and was immediately emulsified to form a satisfactory drink formulation. The emulsified phase was present as small droplets distributed evenly throughout the drink to give satisfactory slightly cloudy homogeneous appearance. No oily slick of ibuprofen was formed. The formulation was allowed to cool slightly and was then ready for administration to the patient as a drink. The emulsion was maintained on cooling (e.g. over 30 minutes).

EXAMPLE 4

On the addition of 200 ml boiling water, a satisfactory coarse emulsion was formed with the majority of the emulsified ibuprofen phase located in the upper portion of the drink. No oily slick of ibuprofen was present on the surface of the drink.

EXAMPLE 5

On the addition of 200 ml boiling water, a satisfactory coarse emulsion was formed with the majority of the emulsified ibuprofen phase located in the upper portion of the drink. No oily slick of ibuprofen was present. Excess egg lecithin was also visible at the surface.

EXAMPLES 6–11

The following actives were mixed as a dry powder with the granular mixture of Example 1.

| Ingredients | Ex 6 | Ex 7 | Ex 8 | Ex 9 | Ex 10 | Ex 11 |
|---|---|---|---|---|---|---|
| Example 1 composition | 3.7 g | 3.7 g | 3.7 g | 3.7 g | 3.7 g | 3.7 g |
| Vitamin C | 150 mg | — | — | — | — | — |
| Pseudoephedrine HCl | — | 30 mg | — | — | — | — |
| Codeine phosphate | — | — | 30 mg | — | — | — |
| Caffeine | — | — | — | 50 mg | — | — |
| Triprolidine HCl | — | — | — | — | 10 mg | — |
| Guaiphenesin | — | — | — | — | — | 200 mg |

Results

The Example mixtures were separately placed into cups and 200 ml hot (>90° C.) water added. The ibuprofen melted and was immediately emulsified to form a satisfactory drink formulation. The emulsified phase was present as small droplets distributed evenly throughout the drink to give satisfactory slightly cloudy homogeneous appearance. No oily slick of ibuprofen was formed. The formulation was allowed to cool slightly and was then ready for administration to the patient as a drink. The emulsion was maintained on cooling (e.g. over 30 minutes).

EXAMPLE 12

In each of Examples 1–11, sorbitol may be used in replacement for the sugar.

EXAMPLE 13

In each of Examples 1–12 malic acid may be used in replacement for citric acid.

EXAMPLE 14

Each of Examples 1–13 may omit the sodium lauryl sulphate.

EXAMPLE 15

Each of Examples 1–14 may contain 100 mg, 300 or 400 mg racemic ibuprofen or S(+)-ibuprofen in replacement for the 200 mg ibuprofen.

EXAMPLE 16

The following composition may also be prepared as described in Example 1.

| | |
|---|---|
| Ibuprofen | 200 mg |
| Citric Acid | 500 mg |
| Soybean lecithin | 10 mg |
| Microcrystalline cellulose | 500 mg |

What is claimed is:

1. A solid ibuprofen composition which, on the addition of water, is capable of yielding an aqueous preparation, said composition consisting essentially of
    (a) one or more medicaments including an ibuprofen medicament which forms an ibuprofen active ingredient having a melting point less than 100° C. when combined with water to give an aqueous preparation having a pH of less than 7,
    (b) a phospholipid material intimately mixed with the ibuprofen medicament and in a ratio to said ibuprofen medicament of 0.001:1 to 0.5:1 parts by weight;
    (c) an acidic component in a ratio to said ibuprofen medicament of 1:20 to 20:1 parts by weight; and
    (d) a water-soluble carrier component;
    wherein, on the addition of water, said composition yields an aqueous preparation having a pH of less than 7; and
    said phospholipid material is capable of forming an aqueous preparation comprising
        i) an aqueous phase substantially free of said ibuprofen active ingredient; and
        ii) a discrete phase consisting essentially of said phospholipid material and insoluble pharmacologically active ingredient including said ibuprofen active ingredient.

2. A composition according to claim 1 which, on combination with water at a temperature above the melting point of the ibuprofen active ingredient, is adapted to form an emulsion having a discrete oily phase consisting essentially of said phospholipid material and insoluble pharmaceutically active ingredient including said ibuprofen active ingredient.

3. A composition according to claim 1 which, on combination with water at a temperature in the range 80–100° C., is adapted to form an emulsion having a discrete oily phase consisting essentially of said phospholipid material and insoluble pharmacologically active ingredient including said ibuprofen active ingredient.

4. A composition according to claim 1 characterised in that the ibuprofen active ingredient comprises ibuprofen or S(+)-ibuprofen.

5. A composition according to claim 1 characterised in that the ibuprofen medicament is racemic ibuprofen or S(+)-ibuprofen.

6. A composition according to claim 1 characterised in that the ratio of phospholipid material to ibuprofen medicament is in the range 0.02:1 to 0.2:1 parts by weight.

7. A composition according to claim 6 characterised in that the ratio of phospholipid material to ibuprofen medicament is in the range 0.03 to 0.07 parts by weight.

8. A composition according to claim 1 characterised in that the phospholipid material comprises one or more natural lecithin materials.

9. A composition according to claim 8 characterised in that the phospholipid material comprises soybean lecithin.

10. A composition according to claim 1 wherein the water-soluble carrier component comprises a sugar component.

11. A composition according to claim 1 comprising a further medicament useful in a cough and/or cold remedy including an antihistamine, a cough suppressant, a decongestant, an expectorant, a muscle-relaxant, a vitamin, caffeine and a co-analgesic or a mixture thereof.

12. A unit dose aqueous preparation comprising an aqueous phase and a discreet phase comprising
   (a) in ibuprofen active ingredient having a melting point of less than 100° C.,
   (b) a phospholipid material capable of forming said ibuprofen active ingredient into a discreet phase on combination with water, wherein the ratio of said phospholipid material to ibuprofen medicament is 0.001 to 0.5:1 parts by weight, and
   (c) an acidic component in a ratio to said ibuprofen medicament of 1:20 to 20:1 parts by weight;
   characterised in that the aqueous preparation has a pH of less than 7 and that said aqueous phase is essentially free of said ibuprofen active ingredient and that said discrete phase consists essentially of said phospholipid material and insoluble pharmacologically active ingredient including said ibuprofen active ingredient.

13. An aqueous preparation according to claim 12 characterised in that when the aqueous phase is at a temperature above the melting point of the ibuprofen active ingredient, the discrete oily phase consists essentially of said phospholipid material and liquid ibuprofen active ingredient.

14. An aqueous preparation according to claim 13 characterised in that the ibuprofen active ingredient is ibuprofen or S(+)-ibuprofen.

15. An aqueous preparation according to claim 12 characterised in that the aqueous phase contains a further medicament useful in a cough and/or cold remedy including an antihistamine, a cough suppressant, a decongestant, an expectorant, a muscle-relaxant, caffeine, a vitamin and a co-analgesic or a mixture thereof.

16. An aqueous preparation according to claim 12 characterised in that the discrete phase consists essentially of said phospholipid material and ibuprofen.

17. An aqueous preparation according to claim 12 characterised in that the phospholipid comprises one or more naturally occurring lecithin materials.

18. A process to make a unit dose aqueous preparation comprising an aqueous phase substantially free of ibuprofen and a discrete phase incorporating ibuprofen characterised by the step of combining a solid ibuprofen composition consisting essentially of an intimate mixture of:
   (a) one or more medicaments including an ibuprofen medicament which forms an ibuprofen active ingredient having a melting point less than 100° C. when combined with water to give an aqueous preparation having a pH of less than 7,
   (b) a phospholipid material capable of forming said ibuprofen active ingredient into a discrete phase on combination of the ibuprofen composition with water, wherein the ratio of said phospholipid material to ibuprofen medicament is 0.001 to 0.5:1 parts by weight;
   (c) an acidic component adapted to yield an aqueous preparation having a pH of less than 7, wherein the ratio of said acidic component to ibuprofen medicament is 1:20 to 20:1 parts by weight; and
   (d) a water-soluble carrier component;
   with water, wherein the combination of said water with said ibuprofen composition causes an aqueous preparation having a pH of less than 7 to be formed substantially immediately wherein the discrete phase consists essentially of said phospholipid material and insoluble pharmacologically active ingredient including said ibuprofen active ingredient.

19. A process according to claim 17 to make an aqueous emulsion by combining said ibuprofen composition with water at a temperature above the melting point of the ibuprofen active ingredient.

20. A process according to claim 18 wherein the discrete phase consists essentially of ibuprofen.

21. A process to prepare a solid ibuprofen composition adapted to provide an aqueous preparation having an aqueous phase substantially free of ibuprofen and a discrete ibuprofen phase on the addition of water at a temperature in the range 0–100° C., comprising
   (a) forming an intimate mixture of (1) one or more medicaments, including an ibuprofen medicament which forms an ibuprofen active ingredient having a melting point less than 100° C. on combination of said ibuprofen medicament with water to give an aqueous preparation having a pH of less than 7, with (2) a phospholipid material capable of forming an aqueous preparation comprising an emulsion or dispersion wherein the discrete phase consists essentially of said phospholipid material and insoluble pharmacologically active ingredient, including ibuprofen active ingredient optionally with other excipients, (3) an acidic component, and (4) a water-soluble carrier component; and
   (b) formulating said mixture into a dose unit composition, wherein the ratio of said phospholipid material to ibuprofen medicament is 0.001 to 0.5:1 parts by weight, and wherein the ratio of said acidic component to ibuprofen medicament is 1:20 to 20:1 parts by weight.

22. A method of obtaining an anti-inflammatory, analgesic and/or anti-pyretic response, comprising administering to a person in need thereof a unit dose aqueous preparation according to claim 12.

23. A process for the preparation of said aqueous preparation comprising adding water to the solid ibuprofen composition according to claim 1.

24. A process according to claim 23 wherein the water is cold or hot water.

25. A solid ibuprofen composition which, on the addition of water, is capable of yielding an aqueous preparation, said composition consisting essentially of
   (a) one or more medicaments including an ibuprofen medicament which forms an ibuprofen active ingredient having a melting point less than 100° C. when combined with water to give an aqueous preparation having a pH of less than 7;
   (b) a phospholipid material intimately mixed with the ibuprofen medicament and in a ratio to said ibuprofen medicament of 0.001:1 to 0.5:1 parts by weight;
   (c) an acidic component in a ratio to said ibuprofen medicament of 1:20 to 20:1 parts by weight;
   (d) a water-soluble carrier component; and
   (e) a non-phospholipid surfactant;
   wherein, on the addition of water, said composition yields an aqueous preparation having a pH of less than 7; and said phospholipid material is capable of forming an aqueous preparation comprising i) an aqueous phase substantially free of said ibuprofen active ingredient; and ii) a discrete phase consisting essentially of said phospholipid material and insoluble pharmacologically active ingredient including said ibuprofen active ingredient.

26. A process to make a unit dose aqueous preparation comprising an aqueous phase substantially free of ibuprofen and a discrete phase incorporating ibuprofen characterised by the step of combining a solid ibuprofen composition consisting essentially of an intimate mixture of:

(a) one or more medicaments including an ibuprofen medicament which forms an ibuprofen active ingredient having a melting point less than 100° C. when combined with water to give an aqueous preparation having a pH of less than 7, (b) a phospholipid material capable of forming said ibuprofen active ingredient into a discrete phase on combination of the ibuprofen composition with water, wherein the ratio of said phospholipid material to ibuprofen medicament is 0.001 to 0.5:1 parts by weight;

(c) an acidic component adapted to yield an aqueous preparation having a pH of less than 7, wherein the ratio of said acidic component to ibuprofen medicament is 1:20 to 20:1 parts by weight;

(d) a water-soluble carrier component; and (e) a non-phospholipid surfactant;

with water, wherein the combination of said water with said ibuprofen composition causes an aqueous preparation having a pH of less than 7 to be formed substantially immediately wherein the discrete phase consists essentially of said phospholipid material and insoluble pharmacologically active ingredient including said ibuprofen active ingredient.

27. A process to prepare a solid ibuprofen composition adapted to provide an aqueous preparation having an aqueous phase substantially free of ibuprofen and a discrete ibuprofen phase on the addition of water at a temperature in the range 0–100° C., comprising (a) forming an intimate mixture of (1) one or more medicaments, including an ibuprofen medicament which forms an ibuprofen active ingredient having a melting point less than 100° C. on combination of said ibuprofen medicament with water to give an aqueous preparation having a pH of less than 7, with (2) a phospholipid material capable of forming an aqueous preparation comprising an emulsion or dispersion wherein the discrete phase consists essentially of said phospholipid material and insoluble pharmacologically active ingredient, including ibuprofen active ingredient optionally with other excipients, (3) an acidic component, (4) a water-soluble carrier component and (5) a non-phospholipid surfactant; and (b) formulating said mixture into a dose unit composition, wherein the ratio of said phospholipid material to ibuprofen medicament is 0.001 to 0.5:1 parts by weight, and wherein the ratio of said acidic component to ibuprofen medicament is 1:20 to 20:1 parts by weight.

28. A solid ibuprofen composition which, on the addition of water, is capable of yielding an aqueous preparation, said composition consisting essentially of (a) one or more medicaments including an ibuprofen medicament which forms an ibuprofen active ingredient having a melting point less than 100° C. when combined with water to give an aqueous preparation having a pH of less than 7;

(b) a phospholipid material intimately mixed with the ibuprofen medicament and in a ratio to said ibuprofen medicament of 0.001:1 to 0.5:1 parts by weight;

(c) an acidic component in a ratio to said ibuprofen medicament of 1:20 to 20:1 parts by weight;

(d) a water-soluble carrier component; and (e) a sweetening agent, flavoring agent, coloring agent or mixture thereof;

wherein, on the addition of water, said composition yields an aqueous preparation having a pH of less than 7; and said phospholipid material is capable of forming an aqueous preparation comprising i) an aqueous phase substantially free of said ibuprofen active ingredient; and ii) a discrete phase consisting essentially of said phospholipid material and insoluble pharmacologically active ingredient including said ibuprofen active ingredient.

29. A process to make a unit dose aqueous preparation comprising an aqueous phase substantially free of ibuprofen and a discrete phase incorporating ibuprofen characterised by the step of combining a solid ibuprofen composition consisting essentially of an intimate mixture of:

(a) one or more medicaments including an ibuprofen medicament which forms an ibuprofen active ingredient having a melting point less than 100° C. when combined with water to give an aqueous preparation having a pH of less than 7, (b) a phospholipid material capable of forming said ibuprofen active ingredient into a discrete phase on combination of the ibuprofen composition with water, wherein the ratio of said phospholipid material to ibuprofen medicament is 0.001 to 0.5:1 parts by weight;

(c) an acidic component adapted to yield an aqueous preparation having a pH of less than 7, wherein the ratio of said acidic component to ibuprofen medicament is 1:20 to 20:1 parts by weight;

(d) a water-soluble carrier component; and (e) a sweetening agent, flavoring agent, coloring agent or mixture thereof;

with water, wherein the combination of said water with said ibuprofen composition causes an aqueous preparation having a pH of less than 7 to be formed substantially immediately wherein the discrete phase consists essentially of said phospholipid material and insoluble pharmacologically active ingredient including said ibuprofen active ingredient.

30. A process to prepare a solid ibuprofen composition adapted to provide an aqueous preparation having an aqueous phase substantially free of ibuprofen and a discrete ibuprofen phase on the addition of water at a temperature in the range 0–100° C., comprising:

(a) forming an intimate mixture of (1) one or more medicaments, including an ibuprofen medicament which forms an ibuprofen active ingredient having a melting point less than 100° C. on combination of said ibuprofen medicament with water to give an aqueous preparation having a pH of less than 7, with (2) a phospholipid material capable of forming an aqueous preparation comprising an emulsion or dispersion wherein the discrete phase consists essentially of said phospholipid material and insoluble pharmacologically active ingredient, including ibuprofen active ingredient optionally with other excipients, (3) an acidic component, (4) a water-soluble carrier component and (5) a sweetening agent, flavoring agent, coloring agent or mixture thereof; and (b) formulating said mixture into a dose unit composition, wherein the ratio of said phospholipid material to ibuprofen medicament is 0.001 to 0.5:1 parts by weight, and wherein the ratio of said acidic component to ibuprofen medicament is 1:20 to 20:1 parts by weight.

31. A solid ibuprofen composition which, on the addition of water, is capable of yielding an aqueous preparation, said composition consisting essentially of (a) one or more medicaments including an ibuprofen medicament which forms an ibuprofen active ingredient having a melting point less than 100° C. when combined with water to give an aqueous preparation having a pH of less than 7;

(b) a phospholipid material intimately mixed with the ibuprofen medicament and in a ratio to said ibuprofen medicament of 0.001:1 to 0.5:1 parts by weight;

(c) an acidic component in a ratio to said ibuprofen medicament of 1:20 to 20:1 parts by weight;

(d) a water-soluble carrier component;

(e) a non-phospholipid surfactant; and (f) a sweetening agent, flavoring agent, coloring agent or mixture thereof;

wherein, on the addition of water, said composition yields an aqueous preparation having a pH of less than 7; and said phospholipid material is capable of forming an aqueous preparation comprising i) an aqueous phase substantially free of said ibuprofen active ingredient; and ii) a discrete phase consisting essentially of said phospholipid material and insoluble pharmacologically active ingredient including said ibuprofen active ingredient.

32. A process to make a unit dose aqueous preparation comprising an aqueous phase substantially free of ibuprofen and a discrete phase incorporating ibuprofen characterised by the step of combining a solid ibuprofen composition consisting essentially of an intimate mixture of:

(a) one or more medicaments including an ibuprofen medicament which forms an ibuprofen active ingredient having a melting point less than 100° C. when combined with water to give an aqueous preparation having a pH of less than 7, (b) a phospholipid material capable of forming said ibuprofen active ingredient into a discrete phase on combination of the ibuprofen composition with water, wherein the ratio of said phospholipid material to ibuprofen medicament is 0.001 to 0.5:1 parts by weight;

(c) an acidic component adapted to yield an aqueous preparation having a pH of less than 7, wherein the ratio of said acidic component to ibuprofen medicament is 1:20 to 20:1 parts by weight;

(d) a water-soluble carrier component;

(e) a non-phospholipid surfactant; and (f) a sweetening agent, flavoring agent, coloring agent or mixture thereof;

with water, wherein the combination of said water with said ibuprofen composition causes an aqueous preparation having a pH of less than 7 to be formed substantially immediately wherein the discrete phase consists essentially of said phospholipid material and insoluble pharmacologically active ingredient including said ibuprofen active ingredient.

33. A process to prepare a solid ibuprofen composition adapted to provide an aqueous preparation having an aqueous phase substantially free of ibuprofen and a discrete ibuprofen phase on the addition of water at a temperature in the range 0–100° C., comprising:

(a) forming an intimate mixture of (1) one or more medicaments, including an ibuprofen medicament which forms an ibuprofen active ingredient having a melting point less than 100° C. on combination of said ibuprofen medicament with water to give an aqueous preparation having a pH of less than 7, with (2) a phospholipid material capable of forming an aqueous preparation comprising an emulsion or dispersion wherein the discreet phase consists essentially of said phospholipid material and insoluble pharmacologically active ingredient, including ibuprofen active ingredient optionally with other excipients, (3) an acidic component, (4) a water-soluble carrier component (5) a non-phospholipid surfactant and (6) a sweetening agent, flavoring agent, coloring agent or mixture thereof; and (b) formulating said mixture into a dose unit composition, wherein the ratio of said phospholipid material to ibuprofen medicament is 0.001 to 0.5:1 parts by weight, and wherein the ratio of said acidic component to ibuprofen medicament is 1:20 to 20:1 parts by weight.

* * * * *